United States Patent [19]

Riebel

[11] Patent Number: 4,736,028

[45] Date of Patent: Apr. 5, 1988

[54] INTERMEDIATE 2-CYANAMINO 1,3,5-TRIAZINE DERIVATIVES

[75] Inventor: Hans-Jochem Riebel, Wuppertal, Fed. Rep. of Germany

[73] Assignee: Bayer Aktiengesellschaft, Leverkusen, Fed. Rep. of Germany

[21] Appl. No.: 851,058

[22] Filed: Apr. 11, 1986

[30] Foreign Application Priority Data

Apr. 27, 1985 [DE] Fed. Rep. of Germany ....... 3515287

[51] Int. Cl.$^4$ ................ C07D 251/42; C07D 251/44; C07D 251/46
[52] U.S. Cl. ................................. 544/194
[58] Field of Search ......................... 544/194

[56] References Cited

U.S. PATENT DOCUMENTS 3,317,528  5/1967  Tsuda et al. .............. 544/194

FOREIGN PATENT DOCUMENTS 2263853  7/1973  Fed. Rep. of Germany ...... 544/194
1052567  12/1966  United Kingdom .

OTHER PUBLICATIONS

Moriya et al., Abstract DE 3334455, published 9/84, (Pergamon, Inpadoc Database).
Organikum, Organisch-Chemisches Grundpraktikum Von Einem Autorenkollektiv der Technischen Universität Dresden (3., uberarbeitete Auflage), Veb Deutscher Verlag Der Wissenschaften, Berlin 1964, p. 389.
Chemical Abstracts, vol. 94, pp. 1 and 656, (May 11, 1981).

Primary Examiner—Henry R. Jiles
Assistant Examiner—J. G. Mullins
Attorney, Agent, or Firm—Sprung, Horn, Kramer & Woods

[57] ABSTRACT

A process for the preparation of a 2-cyanamino-4,6-dialkoxy-1,3,5-triazine of the formula

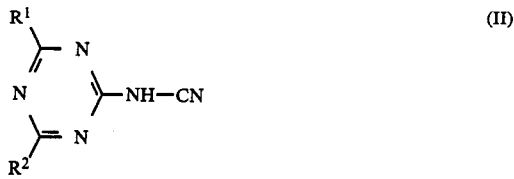

in which $R^1$ and $R^2$ are each alkoxy, which comprises reacting

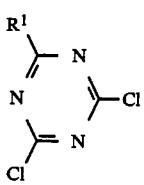

with $Na_2N{-}CN$ to produce

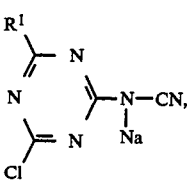

acidifying that to produce

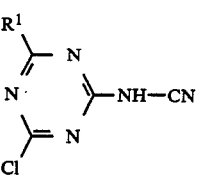

and reacting that with at least twice the molar amount of $R^2Na$ in the presence of a diluent, then adding water and acidifying the mixture.

The intermediates are new and the known end products can be used to synthesize herbicides.

3 Claims, No Drawings

INTERMEDIATE 2-CYANAMINO 1,3,5-TRIAZINE DERIVATIVES

The present invention relates to a new process for the preparation of 2-cyanamino-4,6-dialkoxy-1,3,5-triazines and to new intermediates for this. Some of the process products are known, and they can be used as intermediates for the preparation of herbicides and plant-growth regulators.

It has already been disclosed that 2-cyanamino-1,3,5-triazines are obtained by reaction of alkali metal or alkaline earth metal salts of cyanamide with appropriate 2-halogeno-1,3,5-triazines (compare U.S. Ser. No. 578,345, filed Feb. 9, 1984, still pending/European Pat. No. A-121,082). However, the applicability of this process is only very limited because of the lack of suitable starting compounds or because of unsatisfactory preparation methods for them. Thus, there is a need for widely applicable preparation processes for 2-cyanamino-4,6-dialkoxy-1,3,5-triazines.

It has now been found that 2-cyanamino-2,6-dialkoxy-1,3,5-triazines of the general formula (I)

[Structure of formula (I): triazine ring with $R^1$, $R^2$ substituents and NH—CN group] (I)

in which $R^1$ and $R^2$ are identical or different and represent alkoxy, are obtained when 4-chloro-2-cyanamino-1,3,5-triazines of the formula (II)

[Structure of formula (II): triazine ring with $R^1$, Cl substituents and NH—CN group] (II)

in which $R^1$ has the abovementioned meanings, are reacted with at least twice the molar amount of alcoholate of the formula (III)

$$R^2Me \quad (III)$$

in which
$R^2$ has the abovementioned meanings, and
Me represents one equivalent of an alkali metal ion,
in the presence of diluents, then water is added, and the mixture is acidified.

Surprisingly, it is possible using the process according to the invention to prepare the valuable compounds of the formula (I) in a smooth reaction and in high yields by a simple manner via the new intermediates of the formula (II).

Those compounds of the formula (I) which are preferably prepared using the process according to the invention are those in which $R^1$ and $R^2$ are identical or different and represent alkoxy having 1 to 6 carbon atoms.

Those compounds of the formula (I) which are particularly preferably prepared are those in which $R^1$ and $R^2$ are identical or different and represent methoxy, ethoxy, n-propoxy, i-propoxy, n-butoxy, i-butoxy, sec.-butoxy or tert.-butoxy.

Those compounds of the formula (I) which are very particularly preferably prepared are those in which $R^1$ and $R^2$ are identical or different and represent methoxy, ethoxy, n-propoxy, i-propoxy or n-butoxy.

When, for example, 4-chloro-2-cyanamino-6-methoxy-1,3,5-triazine and sodium methanolate are used as starting materials for the process according to the invention, the reaction can be represented by the equation which follows:

[Reaction scheme: H$_3$CO-triazine-Cl with NH—CN group + 2NaOCH$_3$, −NaCl, −CH$_3$OH → H$_3$CO-triazine-OCH$_3$ with N(Na)—CN group + HCl, −NaCl → H$_3$CO-triazine-OCH$_3$ with NH—CN group]

The 4-chloro-2-cyanamino-1,3,5-triazines which are to be used as starting materials for the process according to the invention are generally defined by the formula (II). Those compounds of the formula (II) in which $R^1$ represents alkoxy having 1 to 6 carbon atoms are preferred.

Those compounds of the formula (II) in which $R^1$ represents methoxy, ethoxy, n-propoxy, i-propoxy, n-butoxy, i-butoxy, sec.-butoxy or tert.-butoxy are particularly preferred.

Those compounds of the formula (II) in which $R^1$ represents methoxy, ethoxy, n-propoxy, i-propoxy or n-butoxy are very particularly preferred.

The compounds of the formula (II) are new. The compounds of the formula (II) are obtained when 2,4-dichloro-1,3,5-triazines of the formula (IV)

[Structure of formula (IV): triazine ring with $R^1$ and two Cl substituents] (IV)

in which $R^1$ has the abovementioned meanings, are reacted with cyanamides of the formula (V), $$(R^3)_2N\text{—}CN \quad (V)$$

in which $R^3$ represents one equivalent of an alkali metal or alkaline earth metal ion, in the presence of water and optionally in the presence of an organic diluent, such as, for example, acetone or acetonitrile, at a pH between 8.5 and 9.5, and at temperatures between −5° C. and +10° C., to give the new compounds of the formula (VI)

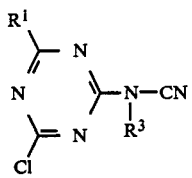
(VI)

in which R¹ and R³ have the abovementioned meanings, and then reacting these compounds of the formula (VI), where appropriate after their isolation, in the presence of water and in the presence of acids such as, for example, hydrochloric acid, at temperatures between −10° C. and +20° C.

The following may be mentioned as examples of starting materials of the formula (II) or (VI): 6-methoxy-, 6-ethoxy-, 6-n-propoxy-, 6-i-propoxy-, 6-n-butoxy-, 6-i-butoxy-, 6-sec.-butoxy- and 6-tert.-butoxy-4-chloro-2-cyanamino-1,3,5-triazine or the corresponding sodium, potassium and calcium salts.

The 2,4-dichloro-1,3,5-triazines to be used as starting materials for the preparation of the compounds of the formula (II) or (VI) are generally defined by the formula (IV). In this formula, R¹ preferably represents those radicals which have been indicated above as being preferred or particularly preferred within the scope of the definition of the substituents in the formula (II).

The following may be mentioned as examples of compounds of the formula (IV): 6-methoxy-, 6-ethoxy-, 6-n-propoxy-, 6-i-propoxy-, 6-n-butoxy-, 6-i-butoxy-, 6-sec.-butoxy- and 6-tert.-butoxy-2,4-dichloro-1,3,5-triazine.

The compounds of the formula (IV) are known or can be prepared in a manner analogous to known processes.

The cyanamides which are also to be used as starting materials for the preparation of the compounds of the formula (II) or (VI) are generally defined by the formula (V). In this formula, R³ preferably represents one equivalent of a sodium, potassium or calcium ion.

The following may be mentioned as examples of compounds of the formula (V): di-sodium cyanamide, di-potassium cyanamide and calcium cyanamide.

The compounds of the formula (V) are generally known compounds of organic chemistry.

The alcoholates which are also to be used as starting materials for the process according to the invention are generally defined by the formula (III). In this formula, R² preferably has those meanings which have been indicated above as being preferred or particularly preferred within the scope of the definition of substituents in the formula (I). In this formula, Me preferably represents a sodium or potassium ion.

The following may be mentioned as examples of compounds of the formula (III): sodium methylate, ethylate, n-propylate, i-propylate, n-butylate, i-butylate, sec.-butylate and tert.-butylate and the corresponding potassium derivatives.

The compounds of the formula (III) are generally known compounds of organic chemistry.

The process according to the invention is carried out in the presence of diluents.

These include, in particular, aliphatic and aromatic hydrocarbons such as pentane, hexane, heptane, cyclohexane, petroleum ether, benzine, ligroin, benzene, toluene and xylene; alcohols such as methanol, ethanol, n-propanol, i-propanol, n-butanol, i-butanol, sec.-butanol and tert.-butanol. The alcohols corresponding to the alcoholates of the formula (III) which are used are preferably employed.

The process according to the invention is generally carried out at temperatures between 0° C. and 50° C., preferably between 0° C. and 40° C. The reactions are generally carried out under atmospheric pressure.

In carrying out the process according to the invention, 2.0 to 2.5 mols, preferably 2.0 to 2.3 mols, of alcoholate of the formula (III) are used for each mol of the compound of the formula (II). The working up of the compounds of the formula (I) is carried out by usual methods. After the addition of the starting materials is complete, stirring is continued for a short time or for several hours at 15° C. to 25° C. The mixture is then evaporated, and water is added to the residue and is acidified with mineral acid such as, for example, hydrochloric acid. The compounds of the formula (I) generally result in the form of crystals.

The 2-cyanamino-4,6-dialkoxy-1,3,5-triazines to be prepared by the process according to the invention can be used as intermediates for the preparation of guanidine derivatives which are active as herbicides and plant-growth regulators (compare EP-OS (European Published Specification) No. 121,082).

PREPARATION EXAMPLES

Example 1

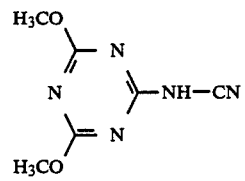

A solution of 1.6 g (0.069 mol) of sodium in 20 ml of methanol is added dropwise, at 20° C. to 30° C., to a suspension of 6 g (0.032 mol) of 4-chloro-2-cyanamino-6-methoxy-1,3,5-triazine in 50 ml of methanol. The mixture is then stirred at 20° C. for 15 hours. The solvent is removed by distillation, and the residue is dissolved in 30 ml of water and acidified with hydrochloric acid. The resulting crystals are filtered off with suction and dried.

5.9 g (92% of theory) of 2-cyanamino-4,6-dimethoxy-1,3,5-triazine are obtained. The product is characterized by ¹H—NMR spectra.

Starting materials of the formula (II)

Example (II-1)

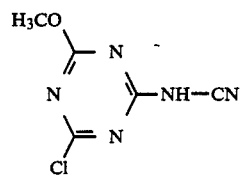

A solution of 9 g (0.043 mol) of 4-chloro-2-cyanamino-6-methoxy-1,3,5-triazine sodium salt in 90 ml of water is acidified with hydrochloric acid and the resulting crystals are then filtered off with suction.

6.7 g (84% of theory) of 4-chloro-2-cyanamino-6-methoxy-1,3,5-triazine, of melting point >260° C., are obtained. The product is characteried by $^1$H—NMR spectra.

Starting materials of the formula (VI)

Example (VI-1)

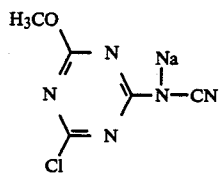

A solution of 17.5 g of disodiumcyanamide in 100 ml of water is added dropwise to a suspension of 36 g (0.2 mol) of 2,4-dichloro-6-methoxy-1,3,5-triazine in 200 ml of ice-water and 20 ml of acetone, at a temperature of 0° C. to 5° C., in such a manner that a pH of 9.5 is not exceeded. Then 40 g of sodium chloride are added and the mixture is stirred at 20° C. for 4 hours.

After filtration with suction and drying, 36.9 (89% of theory) of 4-chloro-2-cyanamino-6-methoxy-1,3,5-triazine sodium salt, of melting point 220° C. (decomposition), are obtained.

It will be understood that the specification and examples are illustrative but not limitative of the present invention and that other embodiments within the spirit and scope of the invention will suggest themselves to those skilled in the art.

I claim:

1. A 4-substituted-2-cyanamino-1,3,5-triazine of the formula

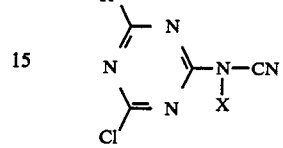

in which
$R^1$ is alkoxy, and
X is H or one equivalent of an alkali metal or alkaline earth metal.

2. A compound according to claim 1, in which X is H.

3. A compound according to claim 1, in which X is one equivalent of an alkali metal or alkaline earth metal.

* * * * *